(12) United States Patent
Ebejer et al.

(10) Patent No.: US 10,532,356 B2
(45) Date of Patent: Jan. 14, 2020

(54) PH CONTROL FOR ANALYTE DETECTION

(71) Applicant: International Business Machines Corporation, Armonk, NY (US)

(72) Inventors: Neil Ebejer, Kilchberg (CH); Patrick Ruch, Tomils (CH)

(73) Assignee: International Business Machines Corporation, Armonk, NY (US)

( * ) Notice: Subject to any disclaimer, the term of this patent is extended or adjusted under 35 U.S.C. 154(b) by 83 days.

(21) Appl. No.: 15/808,138

(22) Filed: Nov. 9, 2017

(65) Prior Publication Data
US 2019/0134632 A1 May 9, 2019

(51) Int. Cl.
*B01L 3/00* (2006.01)
*C02F 1/461* (2006.01)
*C02F 1/00* (2006.01)

(52) U.S. Cl.
CPC ... *B01L 3/502769* (2013.01); *B01L 3/502761* (2013.01); *C02F 1/001* (2013.01); *C02F 1/4618* (2013.01); *B01L 2300/0867* (2013.01); *B01L 2300/0887* (2013.01)

(58) Field of Classification Search
CPC .............................. C25B 1/02; B01L 2200/027
See application file for complete search history.

(56) References Cited

U.S. PATENT DOCUMENTS

| 7,598,064 B2 | 10/2009 | Lee et al. |
| 8,114,261 B2 | 2/2012 | Lee et al. |
| 8,343,330 B2 | 1/2013 | Lee et al. |
| 8,808,519 B2 | 8/2014 | Trubey |
| 2002/0022261 A1 | 2/2002 | Anderson et al. |

(Continued)

FOREIGN PATENT DOCUMENTS

| CN | 103534585 A | 1/2014 |
| CN | 105190302 A | 12/2015 |

(Continued)

OTHER PUBLICATIONS

Minnella, W., "pH Control in MicroFluidics: A Short Review," Elveflow Microfluidics Tutorials, printed: Sep. 27, 2017, pp. 1-10. http://www.elveflow.com/microfluidic-tutorials/cell-biology-imaging-reviews-and-tutorials/microfluidic-for-cell-biology/ph-monitoring-in-microfluidics-a-short-review/.

(Continued)

*Primary Examiner* — Luan V Van
*Assistant Examiner* — Caitlyn Mingyun Sun
(74) *Attorney, Agent, or Firm* — James L. Olsen

(57) ABSTRACT

Aspects of the present disclosure are directed to a pH control device. The device comprises a substrate, on which is defined a flow path adapted to receive a liquid. The device further comprises a set of electrodes, which includes a pH sensing electrode and pH generation electrodes. The electrodes are arranged along the flow path. The pH sensing electrode is arranged so as to be subjected to a change in pH of a portion of the liquid on the flow path, as caused by the pH generation electrodes. In addition, the device includes a controller, which is configured to apply a voltage across the pH generation electrodes, based on a signal obtained via the pH sensing electrode and a reference electrode. This enables local control a pH of the liquid portion. The device may further be embodied as a sensor, additionally comprising a detection electrode.

5 Claims, 8 Drawing Sheets

(56) References Cited

U.S. PATENT DOCUMENTS

| | | | |
|---|---|---|---|
| 2005/0026134 A1 | 2/2005 | Miller et al. | |
| 2005/0233198 A1 | 10/2005 | Nuzzo et al. | |
| 2009/0205974 A1* | 8/2009 | Sivan | B01D 15/3804 |
| | | | 205/701 |
| 2018/0224397 A1* | 8/2018 | Kroll | G01N 27/302 |

FOREIGN PATENT DOCUMENTS

| | | |
|---|---|---|
| CN | 107754874 A * | 3/2018 ........... B01L 3/00 |
| EP | 1748340 A2 | 1/2007 |
| WO | 2010016431 A1 | 2/2010 |
| WO | 2012018777 A1 | 2/2012 |
| WO | 2015000769 A1 | 1/2015 |
| WO | 2017027477 A1 | 2/2017 |
| WO | 2019092531 A1 | 5/2019 |

OTHER PUBLICATIONS

Pasta et al., "A new approach to glucose sensing at gold electrodes," Electrochemistry Communications, vol. 12, Issue 10, Oct. 2010, pp. 1407-1410.

Macounova et al., "Generation of Natural pH Gradients in Microfluidic Channels for Use in Isoelectric Focusing," Analytical Chemistry, vol. 72, No. 16, Aug. 15, 2000, pp. 3745-3751.

Written Opinion of the International Searching Authority, International Application No. PCT/IB2018/058244, dated Jan. 30, 2019, 10 pages.

Suzuki et al., "Integrated microfluidic system for the simultaneous determination of ammonia, creatinine and urea", Sensors and Actuators B: Chemical, vol. 108, Issues 1-2, Jul. 22, 2005, Abstract Only, 2 pages.

Bourilkov et al., "Electrical pH control in aqueous solutions", Jan. 11, 1999, Abstract Only, 3 pages.

Ebejer et al., "pH Control for Analyte Detection", U.S. Appl. No. 16/459,658, filed Jul. 2, 2019.

Ebejer et al., "pH Control for Analyte Detection", U.S. Appl. No. 16/459,660, filed Jul. 2, 2019.

IBM, List of IBM Patents or Patent Applications Treated as Related, Jun. 24, 2019, 2 pages.

* cited by examiner

PH CONTROL FOR ANALYTE DETECTION

BACKGROUND

The present disclosure relates generally to the field of sensors and, in particular, to biosensors.

Biosensors interact with biological molecules (e.g., proteins, sugars, ribonucleic acids, etc.) to obtain data about the physiological state of individuals. To do so, biosensors include detectors (e.g., sensor capable of analyzing physicochemical, optical, piezoelectric, electrochemical, etc. characteristics associated with biomolecules). The data collected by the biosensor can be analyzed to make determinations regarding treatment plans, preventative measure, and the like.

SUMMARY

Aspects of the present disclosure are directed to a pH control device. The device comprises a substrate, on which is defined a flow path adapted to receive a liquid. The device further comprises a set of electrodes, which includes a pH sensing electrode and pH generation electrodes. The electrodes are arranged along the flow path. The pH sensing electrode is arranged so as to be subjected to a change in pH of a portion of the liquid on the flow path, as caused by the pH generation electrodes. In addition, the device includes a controller, which is configured to apply a voltage across the pH generation electrodes, based on a signal obtained via the pH sensing electrode and a reference electrode. This enables local control a pH of the liquid portion. The device may further be embodied as a sensor, additionally comprising a detection electrode.

The above summary is not intended to describe each illustrated embodiment or every implementation of the present disclosure.

BRIEF DESCRIPTIONS OF THE DRAWINGS

Figure 10:
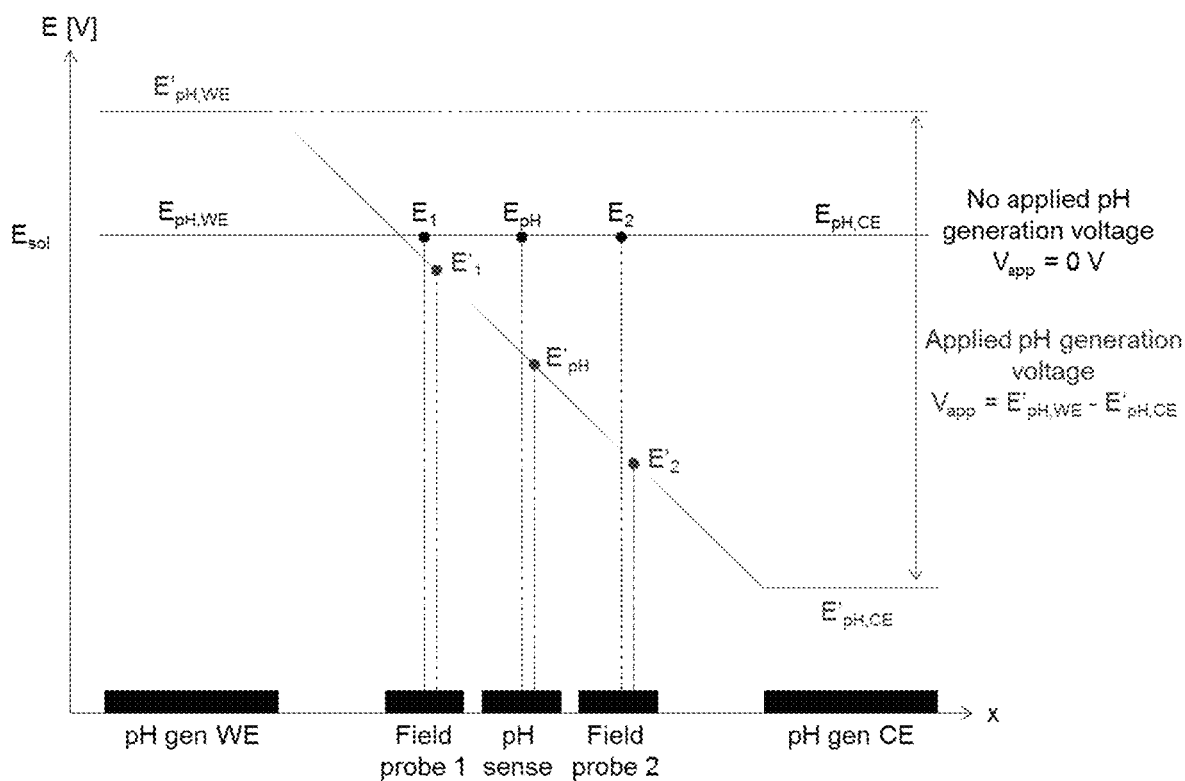
Figure 11:
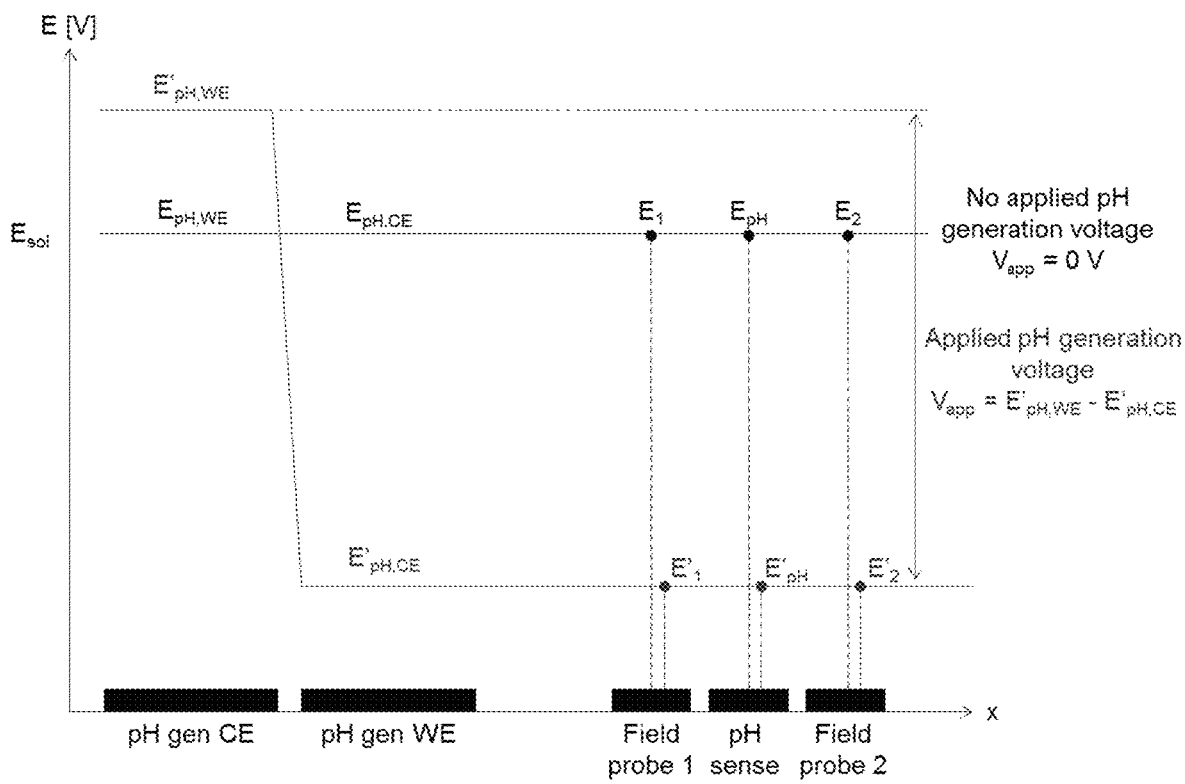

FIGS. 10 and 11 exemplify two possible distributions of electrochemical potential in a liquid solution, with respect to a particular arrangement of electrodes, as involved in embodiments.

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION

Biosensors interact with biological molecules (e.g., proteins, sugars, ribonucleic acids, etc.) to obtain data about the physiological state of individuals. To do so, biosensors include detectors (e.g., sensor capable of analyzing physicochemical, optical, piezoelectric, electrochemical, etc. characteristics associated with biomolecules). Obtaining data regarding the physiological state of individuals allows a vast range of health and medical applications (e.g., prescribing treatment plans). Unfortunately, biosensors are typically not designed for use over extended periods of time. This prevents consistent collection of statistically relevant data and makes it difficult to determine the normal physiological state of an individual.

Biosensors can be constructed on microfluidic chips. Microfluidics enable the precise control and manipulation of small volumes of fluids that are typically constrained to micrometer-length scale channels. Prominent features of microfluidics originate from the behavior that liquids exhibit at the micron scale. Flow of liquids in microfluidics is typically laminar. Volumes well below one nanoliter can be attained by fabricating structures with lateral dimensions in the micrometer range. Microfluidic devices generally refer to microfabricated devices, which are used for pumping, sampling, mixing, analyzing and dosing liquids.

Many microfluidic devices have user chip interfaces and closed flow paths. Closed flow paths facilitate the integration of functional elements (e.g., heaters, mixers, pumps, UV detector, valves, etc.) into one device while minimizing complications associated with open systems (e.g., leaks, evaporation, contamination, etc.). The analysis of liquid samples often requires a series of steps (e.g., filtration, dissolution, heating, washing, reading of signal, etc.).

There are several reasons for the low availability of biosensors for continuous use in devices (e.g., wearables). These factors include cost, complexity of use, inconvenience, and lack of means to store and process the measurement data. All the more, a major obstacle to the continuous use of biosensors is due to the degradation or depletion of biochemical agents (such as proteins) involved in the sensing operations.

Based on the aforementioned, an approach is needed to design biosensors that is not fundamentally restricted in the duration of use by biochemical agents. Aspects of the present disclosure include an effective approach to enable an agent-free detection of analytes (e.g., a non-enzymatic detection of bio-analytes) using conventional electrodes (e.g., metallic electrodes) to modify the pH at which analysis is carried out. This can be achieved by locally controlling the pH of a biological fluid once it enters the sensing device. However, it is difficult to locally control the pH of a biological fluid in a microfluidic environment.

Further, an automated device is also desired, so that it can operate in the field without requiring intervention by a human operator, thus allowing for continuous monitoring of liquids such as waste water or drinking water. Embodiments of the present disclosure include an automated pH control device which can be integrated into biosensors.

In embodiments, a sensor is designed which comprises a microfluidic channel, with an inlet and an outlet port, with at least four electrodes suitably placed along the channel to provide in situ control of the pH about the channel. One electrode is sensitive toward pH and, together with a reference electrode, provides a voltage and/or current signal that is used in a feedback loop (e.g., using PID control) with another electrode pair that generates $H^+$ and $OH^-$ ions (electrolysis, water splitting), to thereby control the pH of the analyte solution.

The pH generator is electrocatalytic towards the water splitting reaction, thereby reducing the required power needed for the reaction. Direct control of pH allows for selective detection of different species by altering the surface properties of a sensing electrode or by shifting the redox potential of the analyte. To achieve a non-enzymatic sensing of bio-analytes, at least one sensing electrode is placed between the pH generation electrode pair and close to the pH sensing electrode, preferably between two pH sensing electrodes.

The downstream pH generation electrode provides the counter-ions necessary to neutralize the waste solution, thereby recovering the initial pH of the biological fluid by means of an appropriate mixing basin.

Figure 1:
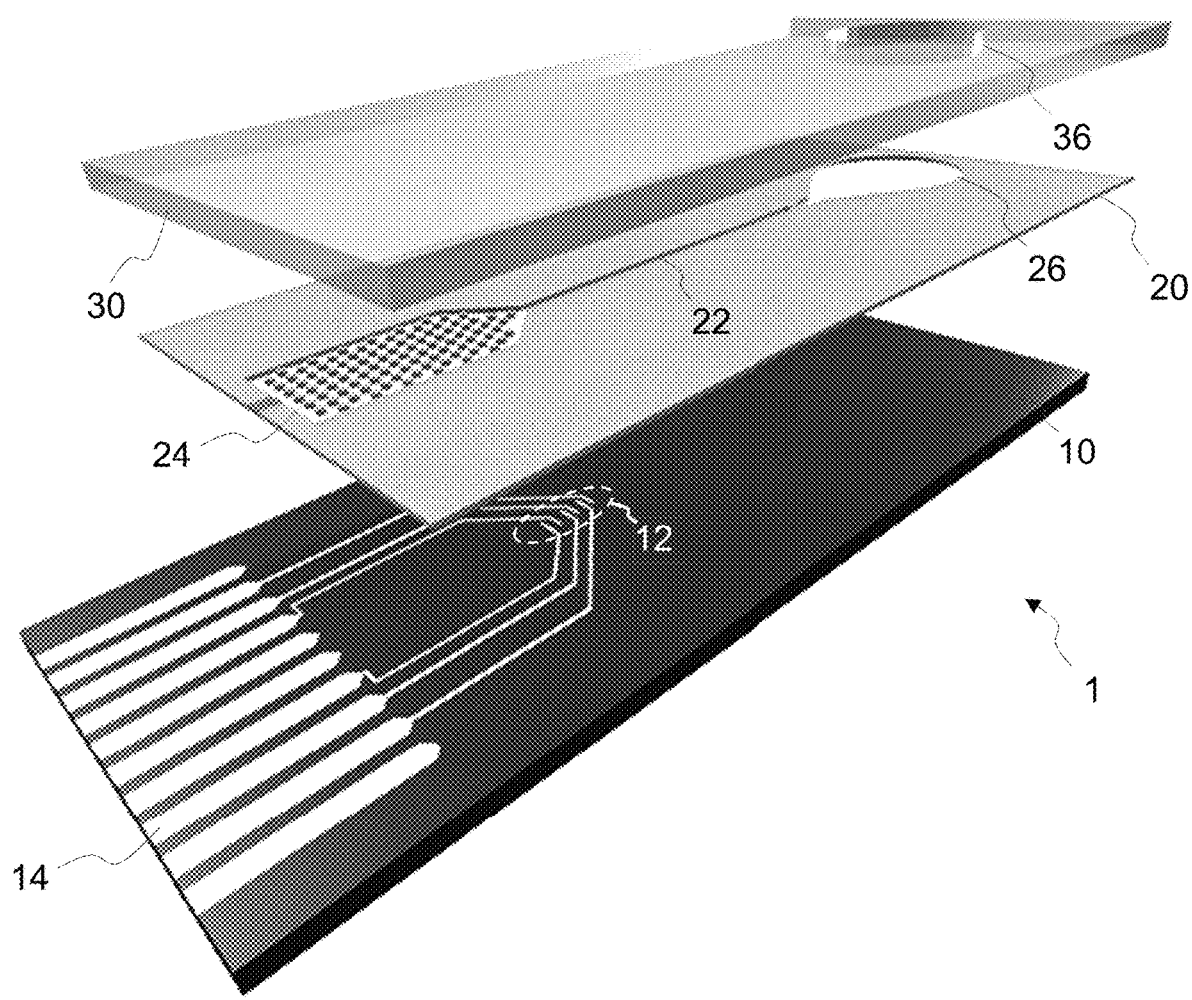
FIG. 1 is an exploded view of a pH control device, in accordance with embodiments of the present disclosure.

FIG. 1 is an exploded view of a pH control device 1, in accordance with embodiments of the present disclosure. The pH control device 1 includes three layers, a substrate 10, a structured middle layer 20, and a structured upper layer 30. The different layers allow various functionalities respective to each layer. For example, the substrate 10 can be formed from a conducting (e.g., or semi-conducting) material, such as silicon, glass or metallic wafer. This can allow the substrate 10 to conduct electricity. The substrate 10 can also include a wicking medium (like a fibrous/porous medium such as paper) or a polymer material. The structured middle layer 20 can allow fluid flow, by integrating an inlet port 26, a flow path 22, and a capillary pump 24. The structured upper layer 30 can prevent exposure to the substrate 10 and structured middle layer 20 (e.g., to confine the system), and can include a loading pad 36 which feeds into the inlet port 26 of the structured middle layer.

A liquid sample (e.g., liquid solution containing an analyte or biomolecule) is first disposed into the loading pad 36 of the structured upper layer 30. The liquid sample then feeds into the inlet port 26, and begins flowing through the flow path 22 of the structured middle layer 20. The flow path 22 can allow the liquid sample to flow through a set of electrodes 12 disposed on the substrate 10. In some embodiments, the liquid sample is transported through the flow path 22 by a net fluid motion, such as capillary action, a thermal gradient, bubble generation, or forced convection. For example, as illustrated in FIG. 1, the pH control device 1 includes a capillary pump 24, to allow a net fluid flow through the flow path 22. Alternatively, in some embodiments, the liquid sample is transported by mere diffusion. The flow path width may be sized depending on the selected liquid transport, to optimize fluid flow and allow sufficient exposure to the set of electrodes 12.

As the liquid sample containing the analyte of interest traverses the flow path 22, the liquid sample passes a set of electrodes 12. The set of electrodes 12 can include electrodes to modify the pH of the liquid sample. Further the set of electrodes can include electrodes to sense the pH which resulted from the change to allow fine tuning of the pH of the liquid sample (e.g., by disposing another electrode configured to modify the pH after the sensing). Additionally, the set of electrodes 12 can include a detection electrode, in order to detect the presence (e.g., concentration) of a biomolecule of interest. In order to properly power the set of electrodes 12, the set of electrodes 12 receive power from electrical connectors 14, which may receive power from an electrical power source (e.g., a battery or industrially provided power).

In some embodiments, the flow path 22 surface may be salinized, to achieve wetting surfaces (e.g., any suitable silinating agent may be used to that aim, such as, for example, trimethylchlorosilane, trichloromethylsilane, or trichlorooctylsilane).

We re-iterate that although the terminology "flow path" is used throughout this description, the present devices do not systematically require a net liquid flow. In particular, well-type sensor devices as mentioned above can be contemplated, which do not require a net liquid flow. Rather, the terminology "flow path" as used herein should be understood as meaning a surface or a volume adapted to receive a liquid, which liquid may, if necessary, be set in motion along this surface or volume, or not.

On-chip electrical circuitry is provided on the substrate 10, so as to connect to each electrode of the set 12. The electricity is provided by electrical connectors 14, which may be set in electrical communication with an external controller (e.g., a processing unit), to convey electrical signals between the controller and electrodes, as the latter get wetted by a liquid that continuously fills the flow path 22. In some embodiments, the microfluidic structures are covered by PDMS covers on one or each side of the Si chip. Alternatively, the sensor chips can be made entirely out of glass and/or silicon, or out of polymers.

The areal density of the capillary structures will typically be adapted, based on the liquid, materials and dimensions used. Passive capillary pumps can be implemented for reasons of portability, simplicity and cost. In some alternatives, liquids may be moved by means of active pumping means only. Also, the presence of passive pumping means does not preclude other active pumping and/or liquid injection means. For completeness, a fluid flow may be achieved by other known techniques (e.g., thermal gradients, bubble generation or forced convection). The present device may thus be configured to allow a net motion flow in one or more of the flow paths.

Electrical connectors 14 can be located at an edge of the pH control device 1, to ease electrical connection. The pH control device may further have a form factor that allows it to be easily inserted in a housing of the device. As electrical connectors 14 are provided at an edge of the chip, they allow for direct plugging of the chip upon insertion in the housing of the device. The electrical connectors 14 can be configured as flat contact pads. Contact pads can be standardized (e.g., microSD card, etc.) for better electrical interfacing with standardized peripheral equipment, although other contacts, such as "pogo-pin" spring-loaded contacts or conductive rubber may also be used, which require less area than flat contact pads. Pogo-pin contacts can be located anywhere on the chip, allowing for electrical connection of a socket from a main surface of the chip.

The present disclosure may be implemented in a terminal or be integrated in a wearable device. The overall dimensions of the housing of the device can be less than 25 mm×60 mm×160 mm, for ergonomic reasons.

The processing device may comprise a data processing unit such as a microcontroller, which may be programmed with low-level computer-program instructions. Such a microcontroller can be appropriately connected and programmed to measure voltage signals from and apply voltages to electrodes on the chip, in operation. To that aim, the data processing unit can include analog-to-digital converters (ADCs) suitably connected to a bus of the controller to communicate data signals as needed for operating the chip.

Figure 2:
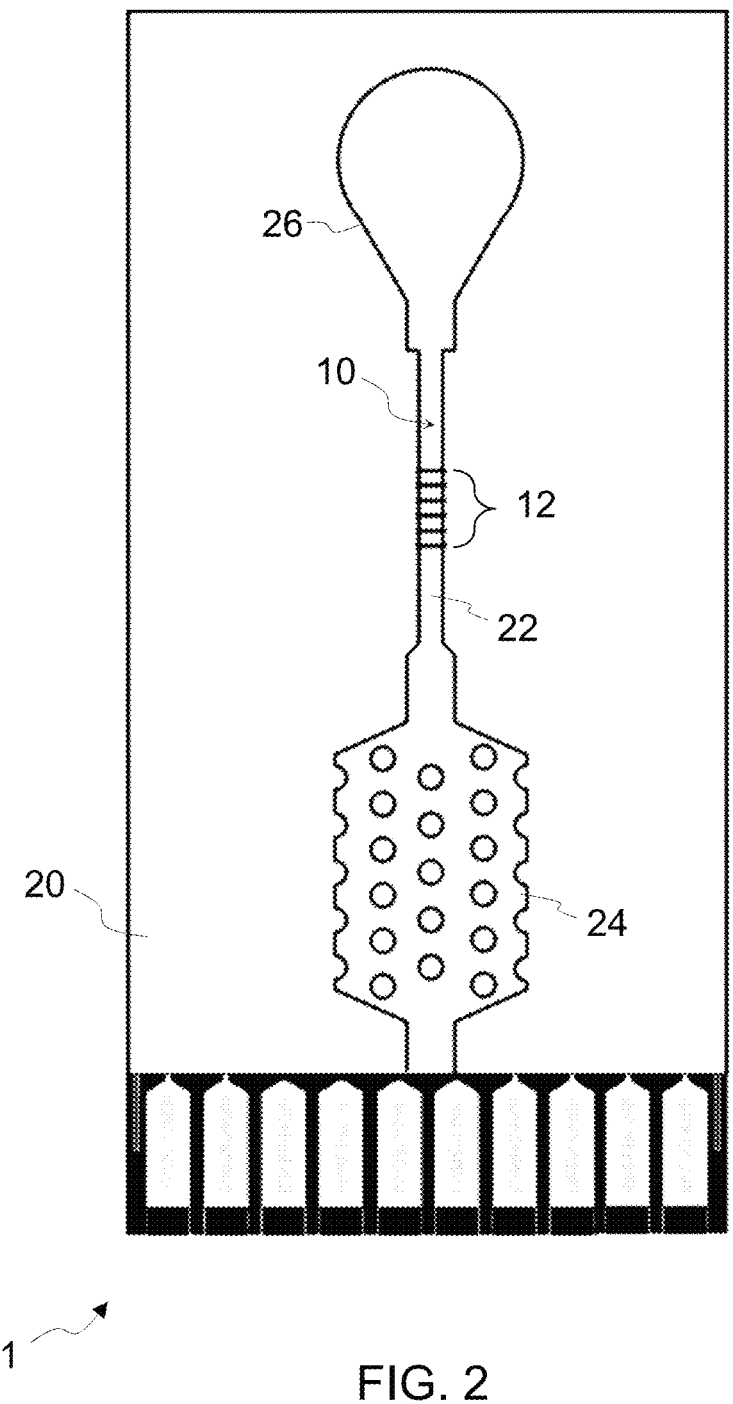
FIG. 2 is a top-down view of a pH control device, in accordance with embodiments of the present disclosure.

FIG. 2 is a top-down view of the pH control device 1 from the structured middle layer 20 (e.g., without the structured upper layer 30 present), in accordance with embodiments of the present disclosure. As referenced and described with respect to FIG. 1, the liquid sample first is disposed into the inlet port 26 (e.g., via loading pad 36 of FIG. 1), which begins fluid flow through the flow path 22 via capillary action by the capillary pump 24. The liquid sample transports through the flow path 22 over the substrate 10 through the set of electrodes 12. The set of electrodes 12 receive power from the electrical connections, and are configured to control the pH of the liquid sample (e.g., via control by a processor based on sensing and a reference signal). In some embodiments, the pH is controlled with PID control, such that the sum of the past errors, present error, and rate of change are considered when controlling the pH of the liquid sample.

Figure 3:
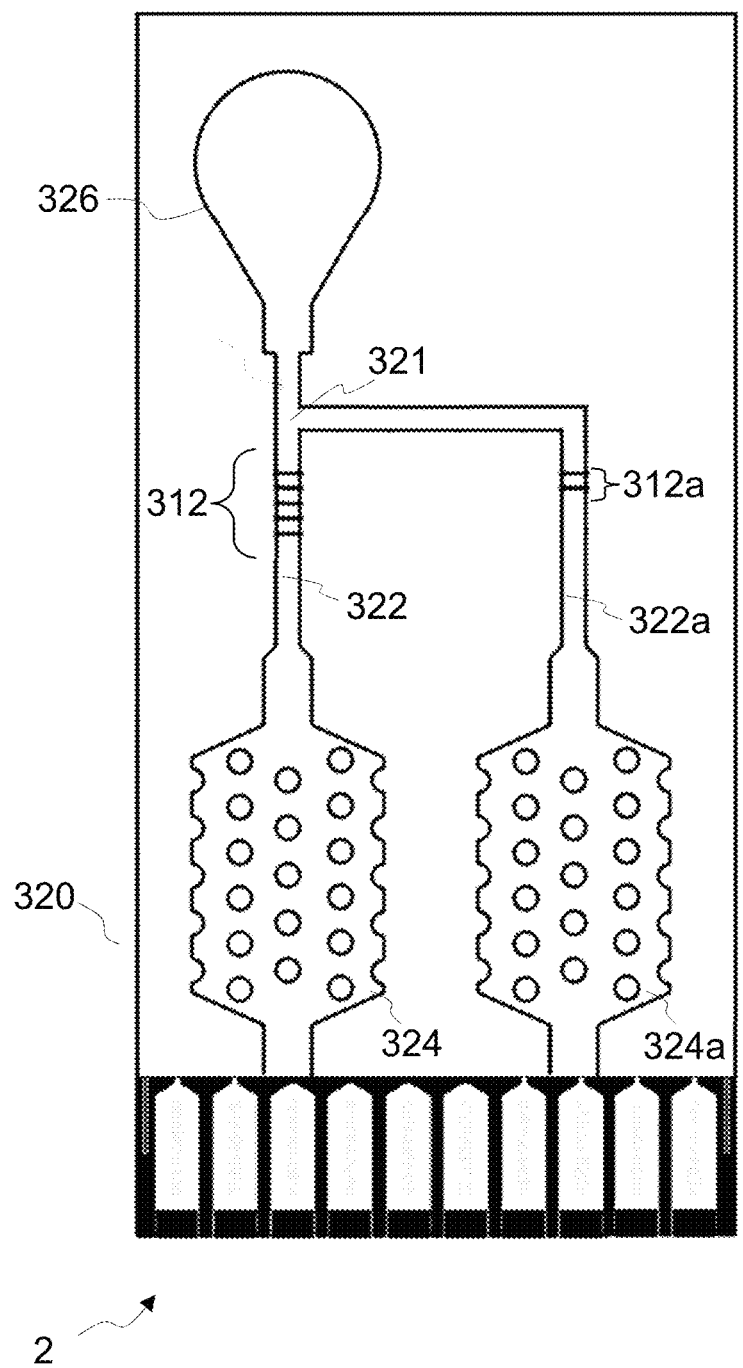
FIG. 3 is a top-down view of a pH control device which includes a first flow path and a second flow path, in accordance with embodiments of the present disclosure.

FIG. 3 is a top-down view of a pH control device 2 which includes a first flow path 322 and a second flow path 322a, in accordance with embodiments of the present disclosure. The illustration of FIG. 3 excludes an upper structured layer (e.g., upper structured layer 30), which may be present, but is not shown, and rather depicts a top-down view from a middle structured layer 320 (e.g., middle structured layer 20 of FIG. 1).

As illustrated in FIG. 3, the pH control device 2 includes the first flow path 322 and the second flow path 322a. Each of the first and second flow paths 322 and 322a are coupled with a first capillary pump 324 and a second capillary pump 324a to drive fluid flow. Vents may be provided on the outer edge of the capillary pumps 324 and 324a, to allow air to escape, while aspirating liquid. Note, however, that the flow paths 322 and 322a may wet the liquid introduced via the loading pad and therefore already sufficiently tract the liquid, without capillary pumps being needed. In variants, other fluid motion means could be involved, as noted earlier.

When the liquid sample enters an inlet port 326 of the structured middle layer 320, the liquid sample encounters a junction 321, which forks the path between the first flow path 322 and second flow path 322a. The liquid sample is then distributed between the first flow path 322 and second flow path 322a. It is noted that the liquid sample may not be evenly distributed between the two flow paths 322, and may depend on the net force driving the fluids, dimensions of the flow paths 322, etc. The liquid entering the first flow path 322 pass through a first set of electrodes 312, and the liquid enter the second flow path 322a pass through a second set of electrodes 312a. The liquid entering the first set of electrodes 312 can be controlled via pH working electrodes (e.g., electrodes that modify the pH of the analyte solution) and pH sensing electrodes.

The second set of electrodes 312a can include a reference electrode to be used as a reference signal for a control loop and/or a reference signal for an analyte detection electrode. Apart from the reference electrode, one or more additional electrodes may be located in proximity of the reference electrode in the second set 312a, in combination with a controller, for verification/measuring purposes. This can be used to implement a feedback loop (e.g., PID control) to control the pH of the liquid sample as necessary. The reference electrode of the second set of electrodes 312a may be located upstream of the first set of electrodes 312, such that the reference signal (e.g., from the reference electrode) is received prior to the counterpart liquid analyte portion entering the first set of electrodes 312.

Though the reference electrode is described as being displaced in the second flow path 322a, in some embodiments, reference electrodes can be disposed in the capillary pumps 324 and 324a. Further, in some embodiments, the first and second set of electrodes 312 and 312a are switched, such that the first set of electrodes 312 is in the second flow path 322a and the second set of electrodes 312a is in the first flow path 322. In some embodiments, the reference electrode is included in the same path as the pH working electrodes and pH sensing electrodes, eliminating the requirement of another flow path (e.g., such as in FIG. 2, for example).

Figure 4:
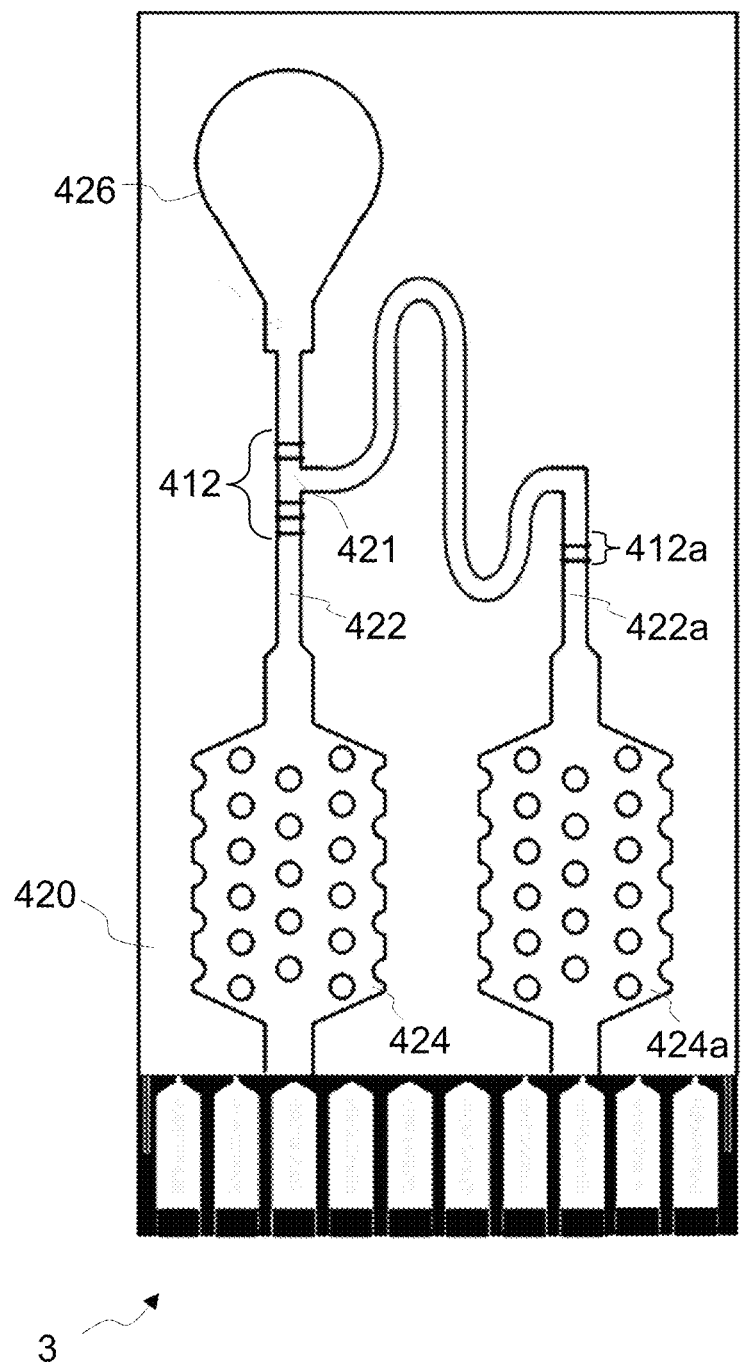
FIG. 4 is a top-down view of a pH control device which includes a first flow path and a second flow path, in accordance with embodiments of the present disclosure.

FIG. 4 is a top-down view of a pH control device 3 which includes a first flow path 422 and a second flow path 422a, in accordance with embodiments of the present disclosure. The illustration of FIG. 4 excludes an upper structured layer (e.g., upper structured layer 30 of FIG. 1), which may be present, but is not shown, and rather depicts a top-down view from a middle structured layer 420 (e.g., middle structured layer 20 of FIG. 1).

As illustrated in FIG. 4, the pH control device 3 includes the first flow path 422 and the second flow path 422a. Each of the first and second flow paths 422 and 422a are coupled with a first capillary pump 424 and a second capillary pump 424a to drive fluid flow. Vents may be provided on the outer edge of the capillary pumps 424 and 424a, to allow air to escape, while aspirating liquid. Note, however, that the flow paths 422 and 422a may wet the liquid introduced via the loading pad and therefore already sufficiently tract the liquid, without capillary pumps being needed. In variants, other fluid motion means could be involved, as noted earlier.

When the liquid sample enters an inlet port 426 of the structured middle layer 420, the liquid sample first passes through two electrodes of a first set of electrodes 412 prior to encountering a junction 421. This allows the liquid analyte pH to be modified (e.g., by a pH generator working electrode) or sensed (e.g., by a pH sensing electrode) prior to entering the junction 421. The liquid analyte is then distributed between the first and second flow paths 422 and 422a, where the liquid analyte passes through the first and second sets of electrodes 412 and 412a. The second set of electrodes 412a can include a reference electrode to reference the pH change of the liquid sample passing through the first set of electrodes 412.

Modifying the pH prior to the junction 421 enables the reference signal of the liquid analyte to reflect a pH modification prior to the fork between the two flow paths 422 and 422a. Accordingly, a feedback loop based on the reference signal can be implemented based on a pre-processed pH modification, in some embodiments. The layout of the sets of electrodes 412 and 412a (e.g., and the sets of electrodes described in FIGS. 1-3) are discussed in greater detail with respect to FIGS. 5-9.

As illustrated in FIG. 4, the second flow path 422a can be curved so as to permit a sufficient distance between the sets of electrodes 412 and 412a and further lower the risk of changes in the composition of the liquid at the reference electrode located in the second set of electrodes 412a. That is, the effective length of the second flow path 422a can be increased, to mitigate effects of ionic diffusion affecting the reference electrode.

Figure 5:
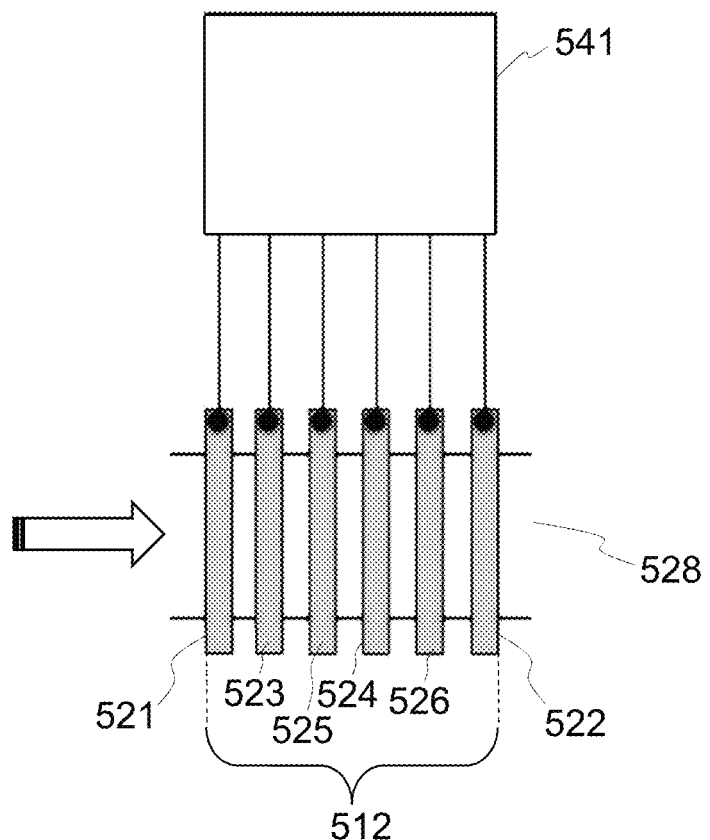
FIG. 5 is a diagram illustrating a set of electrodes that may be implemented a pH control device, in accordance with embodiments of the present disclosure.

FIG. 5 is a diagram illustrating a set of electrodes 512 that may be implemented in one or more of the pH control devices previous discussed (e.g., pH control devices 1-3). The set of electrodes 512 traverses (e.g., superimposes) a flow path 528, such that the liquid analyte transporting through the flow path 528 contacts each electrode of the set of electrodes 512.

The set of electrodes includes a pH generation working electrode (WE) 521, a first pH sensing electrode 523, a detection electrode 525, a second pH sensing electrode 524, a reference electrode 526, and a pH generation counter electrode (CE) 522. The liquid analyte first comes into contact with the pH generation WE 521, which is an electrode configured to receive a voltage (e.g., based on a set-point) from a controller 541 in order to modify the pH of the liquid analyte downstream the flow path 528. The pH of the analyte is then detected by the first pH sensing electrode 523 and/or second pH sensing electrode 524. The pH reported by the first and second pH sensing electrodes 523 and 524 are then fed back into the controller 541 in order to appropriately modify the pH (e.g., in a feedback control loop) by the pH generation WE 521. The liquid analyte biochemical content is analyzed by the detection electrode 525. The detection electrode 525 can be disposed downstream of the pH generation WE 521 in order to ensure the liquid analyte is subject to the desired pH change prior to detection. This can allow accurate analyzation of the liquid analyte and a specific pH or pH range.

After the pH of the liquid analyte is analyzed by the detection electrode 525, the liquid analyte can be neutralized by the pH generation CE 522. The pH generation counter electrode 522 provides the half-cell reaction necessary to neutralize the waste solution, thereby recovering the initial pH of the biological fluid. Neutralization may for instance be achieved thanks to an appropriate mixing basin in the device, contrary to depictions in the accompanying drawings.

In some embodiments, the pH generation WE 521 is positioned upstream areas of interest in the flow path, in order to produce a pH change downstream. For example, the pH sensing electrode 523 can be placed so as to be subjected to a change in pH produced by the pH generation WE 521. The sensing electrode 523 may thus be placed downstream the pH generation WE 521 and upstream the pH generation CE 522, with respect to the liquid analyte advancing in the flow path 528. The first and second pH sensing electrodes 523 and 524 can be adjacent the detection electrode 525.

The pH generation WE 521 and pH generation CE 522 can be configured modify the pH based on a set-point and a pH value reported by the first pH sensing electrode 523 and/or second pH sensing electrode 524. To do so, the pH generation WE 521 and pH generation CE 522 generate hydrogen ions and/or hydroxide ions to decrease and/or increase the pH, respectively.

The chemical reactions believed to be responsible for the change in pH are:

In acidic media:
$2H_2O \rightarrow O_2 + 4H^+ + 4e^-$, at the anode positive terminal, here the pH decreases due to the production of protons; and
$2H^+ + 2e^- \rightarrow H_2$, at the cathode negative terminal, where the pH increases due to the proton consumption; and In basic media:
$4OH^- \rightarrow O_2 + 2H_2O + 4e^-$, at the anode positive terminal, where the pH decreases due to $OH^-$ consumption; and
$2H_2O + 2e^- \rightarrow H_2 + 2OH^-$, at the cathode negative terminal, where the pH increases due to $OH^-$ production.

A current signal indicative of the presence of chemical species may be produced by applying a voltage between the detection electrode 525 and the reference electrode 526. The voltage applied between the detection electrode 525 and the reference electrode 526 may be adjusted so as to impart a pre-defined potential difference between the detection electrode 525 and the reference electrode 526, as is common practice in electrochemistry in three-electrode configurations.

The detection electrode 525 is connected to the controller 541, such that the controller 541 receives signals obtained via the detection electrode 525 and the reference electrode 526, so as to detect chemical species. This way, a sensor is achieved, which is, by design, not restricted by the availability of (bio-)chemical agents, and may advantageously be used for sensing outcomes of pH-dependent chemical reactions, in an autonomous device.

In some embodiments, the first pH sensing electrode 523 is arranged about the flow path 528, between the pH generation WE 521 and the detection electrode 525. The pH sensing electrode 523 may accordingly be placed closer to the pH generation WE 521 and upstream from the detection electrode 525. This way, the pH sensing electrode 523 is able to sense a pH that is relevant to the (downstream) location at which detection occurs, without being too substantially impacted by the reaction occurring about the detection electrode 525. Thus, the pH sensing electrode 523 is not affected by a change in the composition of the liquid that may occur about the detection electrode 525, in operation.

If necessary, two pH sensing electrodes 523 and 524 may be used. For instance, the second pH sensing electrode 524 forms part of the feedback loop (e.g., the controller 541 applies a voltage across the pH generation electrodes 521, 522 based on voltage and/or current signals obtained via electrode pairs formed by each of the sensing electrodes 523, 524 and their associated reference electrode(s)). In a sensor the detection electrode 525 can be arranged between the first pH sensing electrode 523 and the second pH sensing electrode 524, such that pH generation electrodes 523, 524 may be used to more accurately estimate the pH at the level of the detection electrode 525. For instance, the signals obtained from the two pH sensing electrodes 523, 524 may be used for verification or correction purposes at the controller. The two pH values obtained via the sensing electrodes 523, 524 may also be used to extrapolate the pH profile of the liquid along the flow path 528. In variants, the two pH sensing electrodes 523, 524 may be sensitive to different pH ranges.

The design of FIG. 5 relies on a separate reference electrode 526, connected to the controller 541 to serve as a reference electrode for each of the detection electrode 525 and the pH sensing electrodes 523, 524.

In some embodiments, the present pH control and sensor devices comprise several detection electrodes. Two or more detection electrodes may notably be provided to detect distinct chemical species. In variants, the detection electrodes are sensitive toward same species but are used for checking and/or averaging purposes.

The first pH sensing electrode 523, in combination with a reference electrode 526, produces a voltage that is measured by the controller 541, e.g., in order to detect the concentration of hydronium and/or hydroxide ions at the first pH sensing electrode 523.

The voltage obtained via the first pH sensing electrode 523 is further used to determine the voltage to be applied to the pH generation electrodes 521, 522 as part of a control loop, in order to approach a desired pH value.

Thus, the controller 541 can be configured to controllably vary the pH (e.g., the pH does not simply vary, it varies in a controlled manner, in accordance with the feedback loop formed by the sensing electrodes 523, 524, the controller 541 and the pH generation electrodes 521, 522). To that aim, one may for instance use a proportional-integral-derivative controller (PID controller), which calculates a difference between the desired pH set-point and the measured pH and applies a voltage correction based on the observed difference. More generally, any suited processing unit may be used, together with analog-digital converters, to perform the desired operations.

As implicit from the above, the controller 541 is in electrical communication with each electrodes of the set of electrodes 12, though electrodes may be indirectly connected to the controller, via some intermediate electronic components, e.g., for analog-digital conversions, amplification, thresholding, etc.

Only one flow-path 528 is depicted in FIG. 5. However, more complex flow path circuits may be contemplated (e.g., see FIG. 3-4). The liquid to be analyzed may for instance be introduced in one flow path and, at a junction, be re-routed to the flow path along which the set 12 of electrodes are arranged, before being re-routed to a basin, or another flow path, etc., in other embodiments.

The present reference electrodes can be made of a material that ensures a stable potential, such as Ag/AgCl or Pd/H, etc., the purpose being to provide a reference potential against which signals from the pH generation WE 521 or the first pH sensing electrode 523 can be measured. Any reference electrode may further include some protective membrane, as further known per se. In some embodiments, it may be sufficient to employ a simple metallic pseudo-reference (or quasi-reference) electrode such as Ag, Au or Pt as reference electrode, as is often encountered in the field of electrochemistry. Additionally, metallic electrodes may be used for other electrodes (e.g., detection electrode 525 or reference electrode 526), whose materials will typically be selected based on such criteria as: performance with a given analyte, design constraint, fabrication processing (the present electrodes are typically obtained by common photolithography techniques), material compatibilities, etc.

In some embodiments, the reference electrode, which is used in conjunction with the sensing electrode 523 to produce a voltage and/or current signal, may be located in a distinct flow path (e.g., a dead-end channel or another channel). Indeed, the reference electrode 526 may be located sufficiently far from the electrode set 512, so as to minimize its exposure to changes in pH caused by pH generation electrodes 521, 522 (e.g., see FIGS. 3-4). The reference electrode 526 may thus be formed in a separate set of electrodes, as in FIGS. 3-4.

It is noted that the reference electrode 526 can be remotely located, that is, sufficiently far from the set of electrodes 512 such that the liquid composition about the reference electrode 526 is little impacted by ionic diffusion from the liquid portion located between the pH generation electrodes 521, 522.

Apart from the reference electrode 526, one or more additional electrodes may be located in proximity of the reference electrode in a separate set of electrodes (e.g., see FIG. 3-4), also connected to the controller, and used for verification/measuring purposes. The reference electrode 526 located in the district set of electrodes may further serve as a reference for the detection electrode 525 of the set of electrodes 512, in embodiments.

The reference electrode 526 may for instance be located upstream (e.g., in another channel branching upstream from the set of electrodes 512 or between an inlet port and the set of electrodes 512, similar to FIG. 3). In some embodiments, the reference electrode 526 may be located in a channel branching from a main channel (e.g., flow path 422a of FIG. 4).

In some embodiments, only one sensing electrode is present, and the reference electrode 526 serves as a reference voltage for each of the detection electrode 525 and the pH sensing electrode 523. In some embodiments, the reference electrode 526 is arranged between the detection electrode 525 and the pH generation CE 522. In some embodiments, the reference electrode 526 is arranged proximate to the detection electrode 525, in order to improve the accuracy of the electrochemical analysis.

Though the set of electrodes 512 is depicted with individual electrodes in a specific order, any order of electrodes can be implemented, and may depend on the specific analyte to be tested and/or test results sought. Further, any number of electrodes can be implemented. For example, in some embodiments, there may be three or more sensing electrodes. In some embodiments, the sensing electrode 523 may be disposed upstream to the pH generation working electrode 521. In some embodiments, the detection electrode 525 can be disposed adjacent to the pH generation working electrode 521. Further, in some embodiments, combination electrodes can be implemented. That is, in some embodiments, electrodes can be multi-functional, such that the functions of two respective electrodes are combined into a single electrode. For example, a combination electrode can include a hybrid sensing/pH generation electrode. As another example, a combination electrode could include a hybrid pH sensing/analyte detection electrode.

Figure 6:
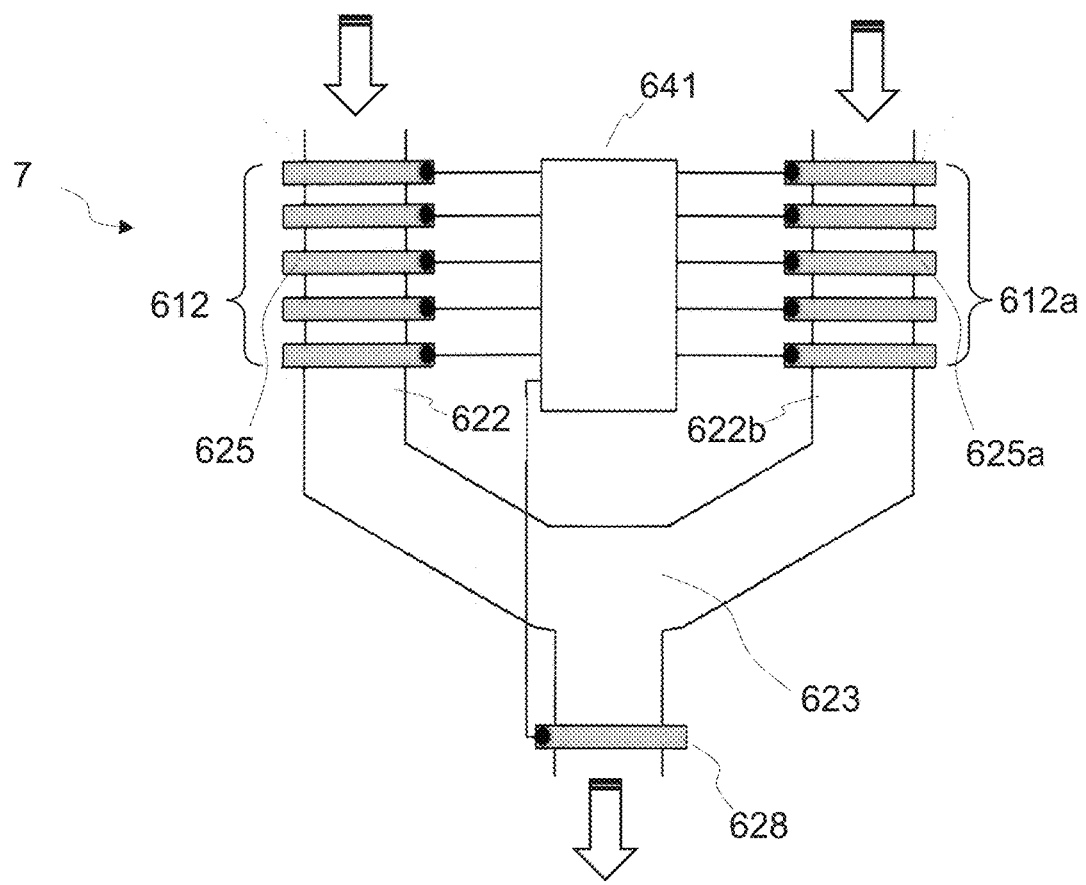
FIG. 6 is a diagram illustrating a first set of electrodes and a second set of electrodes communicatively coupled to a controller, in accordance with embodiments of the present disclosure.

FIG. 6 is a diagram illustrating a pH control device 7 having a first set of electrodes 612 and a second set of electrodes 612a communicatively coupled to a controller 641, in accordance with embodiments of the present disclosure. The first and second sets of electrodes 612 and 612a are illustrated as residing in separate flow paths. Specifically, the first set of electrodes 612 is disposed to superimpose a first flow path 622, and the second set of electrodes 612a is disposed to superimpose a second flow path 622b.

The sets of electrodes 612 and 612a may be the same as, or substantially similar to, the set of electrodes 512 described in FIG. 5 (e.g., including a pH generation working electrode, one or more pH sensing electrodes, a detecting electrode, a reference electrode, and a pH generation counter electrode). As the liquid analyte passes through the flow paths 622 and 622b, the sets of electrodes 612 and 612a are configured to modify the pH based on a control feedback loop and detect an analyte of interest. In some embodiments, the first and second set of electrodes 612 and 612a can detect the same sample, and cross-reference data collected by the counterpart set of electrodes in order to improve testing results.

As illustrated in FIG. 6, the pH control logic can comprise an array of two (or more) detection electrodes 625 and 625a (e.g., respective to each set of electrodes 612 and 612a). Each detection electrode 625, 625a is arranged about a respective flow path 622, 622b. Each detection electrode 625, 625a is further suitably connected to the controller 641, so as to detect chemical species in a liquid on said respective flow paths 622, 622b. (e.g., the controller 641 receives signals from each of the detection electrodes 625, 625a (as well as one or more associated reference electrodes)).

As further seen in FIG. 6, the detection electrodes 625, 625a may belong to respective electrode sets 612 and 612a, each defined about a respective one of the flow paths 622, 622b. The sets of electrodes may for instance comprise, each, one or more pH sensing electrodes and pH generation electrodes. The controller 641 is configured to apply voltages across the resulting pairs of pH generation electrodes, based on voltage and/or current signals obtained via the pH sensing electrodes in each set. Thus, local pH control can be achieved in each flow path 622, 622b.

A pH generation counter electrode may further be provided in each of the electrode sets, as in FIG. 5. However, as illustrated in FIG. 6, a common counter electrode 628 is implemented. Here the flow paths 622, 622b conjoin at a junction 623, downstream of the electrode sets 612, 612a (with respect to upper inlet ports, not shown). The junction 623 is upstream from the pH generation counter electrode 628, the latter configured to serve as a common counter electrode for each of the pH generation working electrodes. This configuration allows the elimination of one of the pH generation counter electrodes (e.g., compared to FIG. 5).

The common pH generation counter electrode 628 may be suitably configured to neutralize liquid downstream the junction 623. Contrary to the depiction of FIG. 6, the common counter electrode may for instance be provided in a mixing basin (not shown), downstream of the junction 623.

In some embodiments, several detection electrodes may be provided in a same set of electrodes, all arranged about a same flow path, with the detection electrodes arranged between the pH generation electrodes, similar to the configuration depicted in FIG. 2.

Figure 7:
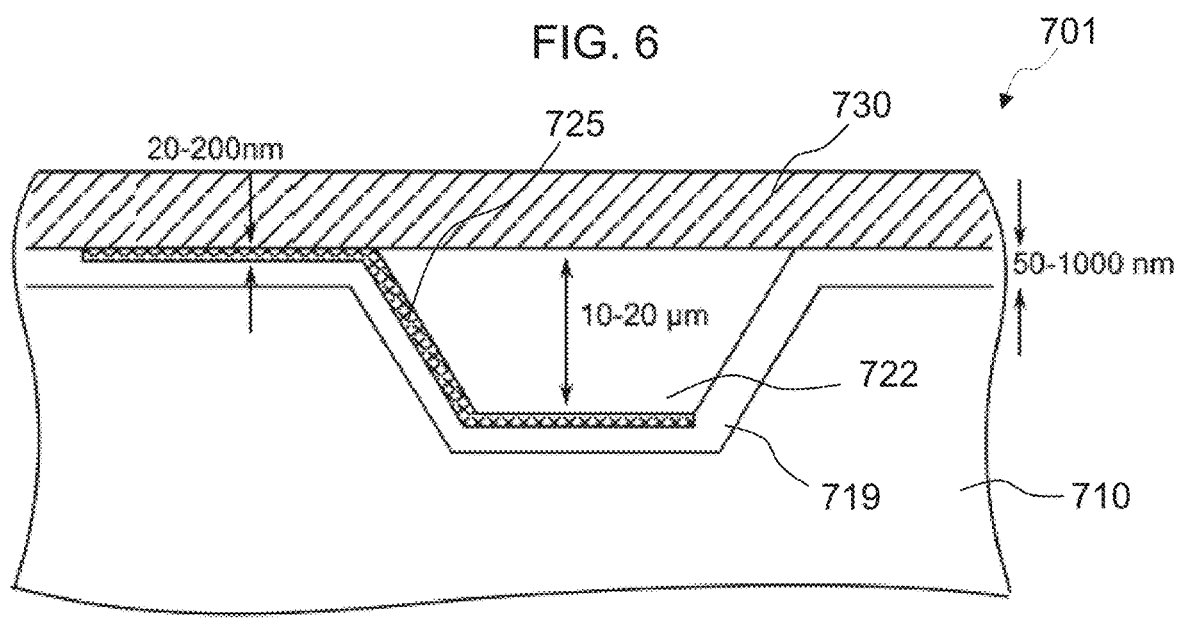
FIG. 7 is a cross-sectional view of a pH control device, in accordance with embodiments of the present disclosure.

Referring now to FIG. 7, shown is a cross-sectional view of a pH control device 701, in accordance with embodiments of the present disclosure. The pH control device 701 includes an upper structured layer 730 disposed on top of a substrate 710. The substrate 710 includes a detection electrode 725, which may be configured to detect the presence of a biochemical species. The detection electrode 725 may be configured to contact a liquid sample passing through a flow path 722 disposed into a middle structured layer (not shown). This can allow the detection electrode 725 to analyze the concentration of an analyte of interest in the liquid sample.

As depicted in FIG. 7 each electrode (which could in fact be any one of the electrodes of the set of electrodes, such as the set of electrodes 512 described in FIG. 5) contacts the flow path 722. This electrode can be fabricated such as to be level with a surrounding surface 719 in the flow path 722. In other words, electrodes may possibly be arranged in the flow path 22 such as to be integrated within a superficial thickness of surfaces of the channel that define the flow path 722, so as for the exposed surfaces of the electrodes to be flush with the surrounding surface 719.

In the example of FIG. 7, the microchannel that defines the flow path 22 exhibits slanted lateral walls. The electrodes are multiwall electrodes, extending at least partly across the surface 719, i.e., over one of the slanted walls, the bottom side of the channel (and, possibly, over the opposite slanted wall too, though not shown), while remaining level with the surrounding surface.

The misalignment between an exposed electrode surface and the surrounding surface is typically negligible with respect to the depth of the microchannel (preferably two or three orders of magnitude below). For instance, fabrication methods are known which can be used to achieve misalignments that are less than 20 nm, and even less than 10 nm, whereas the channel depth may typically be between 10 and 20 μm. This minimizes surface topography and thus favors laminar flows, which may be advantageous to prevent sticking of particles in the liquids analyzed along the flow path. Minimized surface topography can also be advantageous to avoid pinning sites during the initial filling of a flow path by a liquid. This also reduces edge-defects on the electrodes and thus prevents spurious electric fields at the edges of electrodes. This further favors an efficient sealing by the upper structured layer 730.

Several materials can be contemplated for the structured upper layer 730. These materials include glass, PDMS, polymers, or dry-film resists (usually optically clear), such as polyepoxide films. Dry-film resists are notably rigid enough to tent over the flow path 22 without collapsing. They can be easily diced and have good adhesion to the surface to prevent delamination and leaking. In some embodiments, a cover film initially provided as a laminate sheet is implemented to apply it on the surface of the substrate. In variants, any rigid enough cover film (e.g., of the structured upper layer 730) can be contemplated, like silicon or thin glass. If an optical clear material is required, glass can be used.

Electrodes can be dimensioned as follows. Each electrode of the set may have a width w between 10 and 500 μm. The gap g between the electrodes is between 10 and 1000 μm and can larger than the electrodes width w, to minimize perturbations on the liquid flow. Each of the electrodes can have a width between 30 and 160 μm, while the gap between the electrodes can be between 40 and 520 μm. Metal electrodes are typically used, e.g., comprising Pd, Au, Pt, or Ag. Additional electrode materials can be metal oxides such as $MnO_2$ or $NiO_2$, in particular for anodic water splitting, or conductive polymers such as polyaniline or polypyrrole. Also, the electrodes may be implemented in a stacked configuration, such that for example a metallic electrode could be covered with a polymeric material which comprises an ionophore, such that the exposure of the metallic electrode to the analyte solution is restricted. In another example of a stacked configuration, an Ag electrode could be reacted with $FeCl_3$ as a means to achieve a coating of the Ag electrode with AgCl, as known per se.

For chips made of materials other than silicon or glass, for example polymer, the preferred dimensions of the electrodes tend to be larger. For example, the preferred width w of the electrodes on a plastic substrate may be between 500 μm and 2 mm, while the detection counter electrode in particular may be even larger, for example up to 5 mm wide, in order to provide a large electrode area to sustain current flow. Similarly, the gap between the electrodes fabricated on polymer chips can be between 500 μm and 1 mm.

Example dimensions of the flow path 722 are as follows. Each of the microchannels (subtending any of the flow paths described herein) may have a depth that is between 10 and 100 μm. All channels can have the same depth. The width of the channels is typically between 10-500 μm. The inlet port and the capillary pumps can have larger widths. For well-type configurations, the aperture of the well can be between 1-4 mm in diameter.

Such dimensions typically apply to chips, i.e., devices whose core chips are fabricated in silicon or glass, or are injection molded. Devices relying on wicking media would typically differ in dimensions. For example, wax-printed devices can be dimensioned as follows. The minimal (in-plane) width of wax-printed, lateral channel walls may be on the order of 300 μm (as after printing), and 850 μm (after heat treatment, due to the wax spreading). The depth is determined by the thickness of the wicking media (typically larger than 100 μm). The channel width (e.g., the in-plane separation between the wax-printed, lateral walls) may for example be between 100 μm and 1000 μm, with a typical 50 μm standard deviation, after heat treatment.

Figure 8:
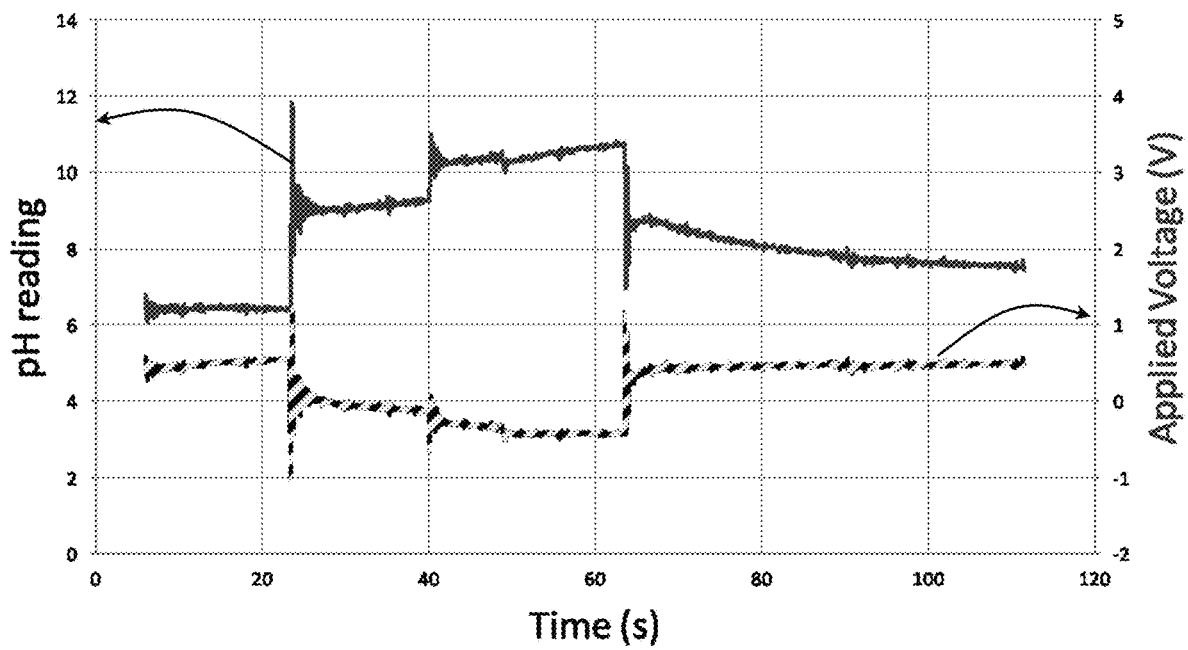
FIG. 8 is a graph illustrating a pH curve over time for a pH control device, in accordance with embodiments of the present disclosure.

FIG. 8 is a graph illustrating a pH curve over time for a pH control device (e.g., pH control device 1). The pH response (upper curve) of a liquid (water), as measured upon applying a voltage (lower curve) across pH generation electrodes of a static microfluidic system having an electrode configuration as depicted in FIG. 5. Note that the water splitting reaction is non-linear once the required potential is reached. Yet, obvious correlations can be seen between the lower and upper curves, showing that pH control can be achieved. Feedback provided by the pH sensing electrodes serves to modulate the voltage applied across pH generation electrodes, so as to achieve and/or maintain a desired pH value in the liquid portion.

Note that different electrode materials may be used, which act more or less catalytically for $H^+$ consumption or generation (in acidic media) or $OH^-$ consumption or generation (in basic media). These materials (e.g., Pt or Pt-alloys for $H^+$ consumption and $MnO_2$ or $NiO_2$ for $H_2O$ splitting, as known from the field of water electrolysis) will be chosen based on the reaction desired. The materials may further be selected so as to limit the electrode output current and hence avoid the formation of bubbles.

Figure 9:
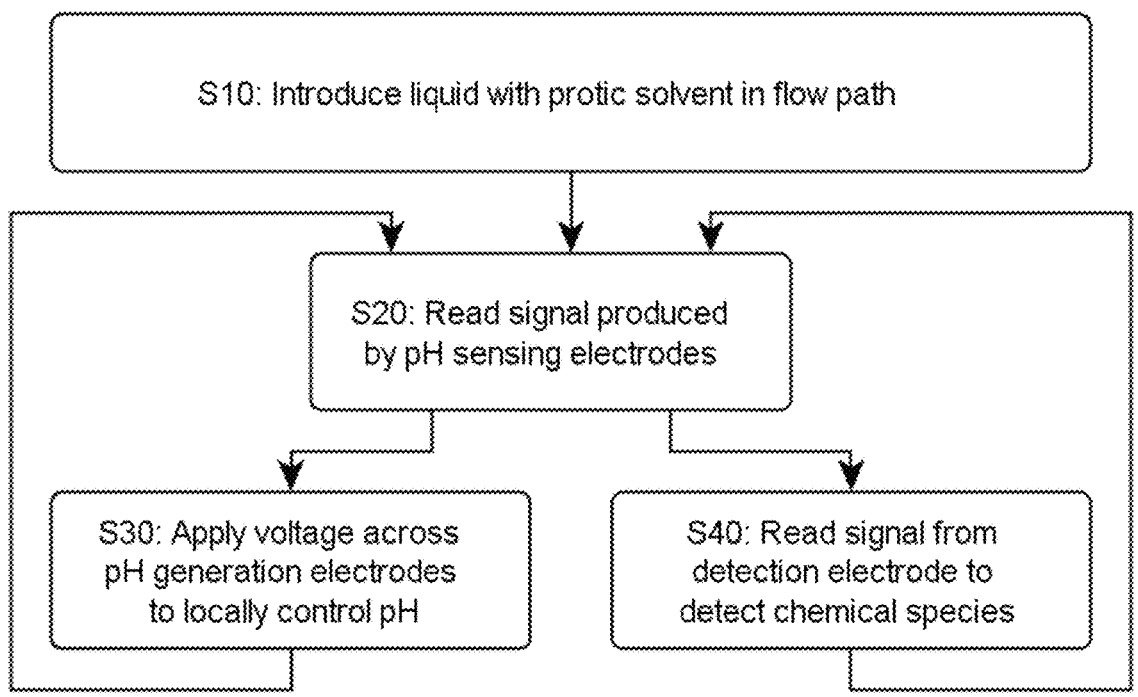
FIG. 9 is a flow diagram illustrating an example method implemented in a pH control device, in accordance with embodiments of the present disclosure.

FIG. 9 is a flow diagram illustrating an example method implemented in a pH control device. The method first includes introducing a liquid comprising a protic solvent on a flow path. This is illustrated at step S10. The method next includes reading (e.g., by a pH sensing electrode) a pH of the protic solvent (e.g., or any other solvent used in the liquid sample). This is illustrated at step S20. At step S30, a voltage is applied across pH generation electrodes to locally control pH. Further, at step S40, read signals from the detection electrodes are used to provide information about chemical species present in the liquid sample.

This pH control method may form part of a method of detection of analytes, according to another aspect of the disclosure. In some embodiments, the controller further reads signals from the detection electrodes to detect chemical species, while applying voltages across pH generation electrodes, based on feedback signals received from the pH sensing electrode and a reference electrode. Both methods may leverage pH control to provoke a reaction.

The above embodiments have been succinctly described in reference to the accompanying drawings and may accommodate a number of variants. Several combinations of the above features may be contemplated.

Further embodiments can be contemplated, which address a practical challenge that may arise with the voltage produced by any of the pH sensing electrodes in combination with a reference electrode, as now discussed in reference to FIGS. 10, 11. FIGS. 10, 11 assume specific electrode configurations, which can be relied on to address such a challenge. When no voltage is applied to any of the electrodes, the electrochemical potential $E_{sol}$ of the liquid solution is constant throughout the device. Therefore, each electrode as depicted in FIG. 10, 11 is exposed to the same solution potential, $E_{sol}=E_{pH,WE}=E_1=E_{pH}=E_2=E_{pH,CE}$. Next, when a voltage $V_{app}=E_{pH,WE}-E'_{pH,CE}$ is applied across the pH generation electrodes, the solution potential experiences a gradient in the space between the two pH generation electrodes. This gradient may ideally correspond to a linear variation, due to a constant electric field strength. As a result, electrodes placed in the space between the pH generation electrodes will be exposed to different electrochemical potentials of the solution and, therefore, provide different voltage readings against a reference electrode. More specifically, the potential of the pH sensing electrode may be affected by the change in solution potential. This change in potential $E_{pH}-E'_{pH}$ (due to the exposure to an electric field within the channel) partially obscures the change in potential of the pH sensing electrode (due to a change in the solution pH), therefore hindering the accurate determination of pH within the channel. As remediation, two additional electrodes (termed field probe electrodes) are placed adjacent to the pH sensing electrode as depicted in FIG. 10, 11. These field probe electrodes may be metallic, e.g., Au or Pt. They may be identical, so that any potential difference arising between these electrodes can be attributed to the presence of a local electric field. By knowledge of $E'_1-E_1$ and $E'_2-E_2$, the quantity $E'_{pH}-E_{pH}$ can be inferred, assuming a linear variation of the solution potential. The quantity $E'_{pH}-E_{pH}$ can then be used to correct the variation in potential of the pH sensing electrode due to electrical field. If each field probe electrode is placed at the same distance on either side of the pH sensing electrode, then $E'_{pH}-E_{pH}=((E'_1-E_1)-(E'_2-E_2))/2$ when there is no pH change, and any deviation from this equation can be attributed to a change in the pH sensing electrode potential due to a pH variation. Maintaining the assumption of constant electric field strength, one may easily derive the expression for asymmetric placement of the field probe electrodes.

The influence of the local electric field can be reduced by arranging the pH generation electrodes adjacent to one another (as in FIG. 11), or by intermittently switching off the pH generation voltage in order to measure the pH sensing electrode potential in an unperturbed state.

Examples of Applications

The following examples focus on analyte detection in aqueous media. In the case of glucose as analyte, pH control allows in situ surface functionalization (e.g., at lower pH the surface of a gold electrode is chloride functionalized but at higher pH the surface groups become hydroxide functionalized, which is reduced electrochemically). It is more favorable for the glucose to bind to this fresh surface and become oxidized. Other catalytic materials (other than gold) may be used to exploit a similar mechanism. Other applications can further be contemplated, which are also pH-dependent, as discussed in the second example below.

A first example concerns glucose sensing in body fluids. It is known that glucose can be directly oxidized on gold surfaces without the need for the enzyme glucose oxidase, provided that the direct oxidation takes place at a pH of 11.5. More specifically, a gold hydroxide, $AuOH_3$, is believed to form spontaneously on gold electrodes at a pH of 11.5. When the potential of the gold electrode is reduced, i.e., made more negative with respect to the potential of a reference electrode, the gold hydroxide is reduced, thereby revealing a pristine gold surface. From this moment on, glucose adsorbed on the gold electrode is immediately oxidized, accompanied by a current flow which can be measured in an external circuit between the gold electrode and a counter electrode, or between the gold electrode and the reference electrode. The magnitude of this oxidation current can be used to quantitatively determine the concentration of glucose, provided the pH is maintained at 11.5. At a lesser pH, for example 5-7, gold is easily passivated through the adsorption of chloride ions on its surface, which prevents the adsorption of glucose molecules which is a critical first step in the direct oxidation of glucose. Both conditions preventing direct glucose oxidation on gold electrodes—a pH of 5-7, as well as the presence of chloride ions—are fulfilled in body fluids. However, as made possible in embodiments of the present disclosure, the pH of the body fluid may be adjusted within the sensing device, for example from 5-7 to 11.5, thereby allowing for the direct oxidation and quantification of glucose in body fluids to take place without requiring enzymatic activity or any additional chemical medium.

Another example concerns the detection of trace metal in water. Anodic stripping voltammetry is a commonly employed analytical technique to determine the concentration of trace metals such as lead, cadmium, zinc or copper in water. The mechanism of detection of these metals on bismuth film electrodes is also known. Furthermore, the stripping voltammetric response, which is the signal used to quantify the amount of trace metals in a water sample, depends on the pH of the analyte solution. The stripping voltammetric response reaches its maximum for a pH of about 4.5. The signal decays both at a lower pH and at a higher pH and notably has been found to vanish at a pH of about 6. Since water samples may often exhibit a pH of 6 or higher, it becomes necessary to add some amount of acid to the sample in order to reduce its pH prior to carrying out the anodic stripping voltammetry measurement. However, as one may realize, the addition of acid is impractical, for small sensors, especially for wearable, remote and/or autonomous sensors. Therefore, embodiments of the present disclosure may be applied to adjust the pH of a water sample and thereby quantitatively detect trace metals by anodic stripping voltammetry, without the need for any addition of acid.

While the present disclosure has been described with reference to a limited number of embodiments, variants and the accompanying drawings, it will be understood by those skilled in the art that various changes may be made and equivalents may be substituted without departing from the scope of the present disclosure. In particular, a feature (device-like or method-like) recited in a given embodiment, variant or shown in a drawing may be combined with or replace another feature in another embodiment, variant or drawing, without departing from the scope of the present disclosure. Various combinations of the features described in respect of any of the above embodiments or variants may accordingly be contemplated, that remain within the scope of the appended claims. In addition, many minor modifications may be made to adapt a particular situation or material to the teachings of the present disclosure without departing from its scope. Therefore, it is intended that the present disclosure not be limited to the particular embodiments disclosed, but that the present disclosure will include all embodiments falling within the scope of the appended claims. In addition, many other variants than explicitly touched above can be contemplated. For example, various other materials could be used in the present devices. As another example, valves, including passive or active microvalves may be contemplated in the present devices, so as to make it possible to periodically aspirate fluids and allow detection thereon.

The present devices can be implemented as sensors (e.g., as wearable sensors) and are preferably fabricated as microfluidic devices. The disclosure may for instance be embodied as a low-cost, easy-to-use, wearable sensor. In some embodiments, the present pH control and sensor devices may be modular, as implemented in a chip and a separate terminal where the chip is inserted in the terminal in operation. In these embodiments, the controller can be implemented at the terminal. In some embodiments, the controller is implemented on-chip.

The configuration of the present devices (including sensor devices as discussed below) allows local pH control of a liquid. In particular, the present approach makes it possible to use conventional metallic electrodes for modifying the pH of a liquid portion at which an analysis is to be carried out.

In turn, the possibility to modify and control the pH of a small liquid section enables chemical reactions that are pH-dependent. This way, a sensor can be designed, based on the above pH control device, which is not restricted in the duration of use. In particular, the present approach opens the door to bio-sensors that are not restricted by the availability of biochemical agents, such as enzymes or organic coatings like membranes.

Embodiments of the present disclosure may notably be directed to chemical assays, such as the detection of trace metals by anodic stripping voltammetry, which typically require an adjustment of pH to be carried out in order to discriminate the analyte from other signals. With conventional analysis methods, this typically requires a manual or automatic addition of the corresponding amount of acid or base from an external reservoir. However, doing so is impractical for miniaturized and integrated applications, e.g., applications to small, wearable or remote sensors, which should instead operate autonomously. Another application concerns glucose detection.

What is claimed is:

1. A pH control device, comprising:
   a substrate,
   a first flow path defined on the substrate adapted to receive a liquid;
   a second flow path defined on the substrate which branches from the first flow path at a junction so as to receive the liquid in operation;
   a set of electrodes located in the first flow path, wherein the set of electrodes comprises:
   a pair of pH generation electrodes, wherein the pair of pH generation electrodes include a pH generation working electrode and a pH generation counter electrode; and
   a pH sensing electrode, wherein the pH sensing electrode is placed downstream of the pH generation working electrode and upstream of the pH generation counter electrode;
   a reference electrode located in the second flow path; and
   a controller,
   wherein:
   the set of electrodes is arranged along the first flow path, the pH sensing electrode arranged so as to be subjected to a change in pH of a portion of the liquid on the first flow path; and
   the controller is configured to apply a voltage across said pH generation electrodes based on a signal obtained via the pH sensing electrode and the reference electrode, so as to modify a pH of the liquid at the pH generation working electrode and the pH generation counter electrode.

2. The pH control device according to claim 1, wherein said pH sensing electrode is placed closer to the pH generation working electrode than the pH generation counter electrode, so as for the sensing electrode to be subjected to a change in a pH of said portion of the liquid that is predominantly caused by the pH generation working electrode.

3. The pH control device according to claim 1, wherein the device further comprises two additional electrodes surrounding the pH sensing electrode to sample a potential gradient across the pH sensing electrode via the additional electrodes.

4. The pH control device according to claim 1, wherein an inlet port is defined on the substrate for loading the liquid in the first flow path and said junction is upstream the pH generation electrodes, between said inlet port and the set of electrodes.

5. The pH control device according to claim 1, wherein said junction is located between the pH generation electrodes.

* * * * *